(12) United States Patent
Berglund et al.

(10) Patent No.: US 7,713,540 B2
(45) Date of Patent: May 11, 2010

(54) DEVICES AND METHODS FOR REVERSE LIPID TRANSPORT

(75) Inventors: Joseph D. Berglund, Santa Rosa, CA (US); Ayala Hezi-Yamit, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 12/033,497

(22) Filed: Feb. 19, 2008

(65) Prior Publication Data

US 2009/0208549 A1    Aug. 20, 2009

(51) Int. Cl.
*A61F 2/00* (2006.01)
*A61M 29/00* (2006.01)

(52) U.S. Cl. .................................. 424/422; 604/96.01
(58) Field of Classification Search .......................... None
See application file for complete search history.

(56) References Cited

U.S. PATENT DOCUMENTS

| | | | |
|---|---|---|---|
| 4,655,744 A | | 4/1987 | Thistle et al. |
| 4,994,025 A | | 2/1991 | DeAntonio et al. |
| 5,746,223 A | * | 5/1998 | Williams .................... 128/898 |
| 6,773,719 B2 | * | 8/2004 | Rodrigueza et al. ......... 424/450 |
| 7,060,051 B2 | * | 6/2006 | Palasis .................. 604/101.01 |
| 2007/0125247 A1 | * | 6/2007 | Kunstmann et al. ......... 101/170 |

OTHER PUBLICATIONS

Rodal et al., "Extraction of Cholesterol with Methyl-B-Cyclodextrin Perturbs Formation of Clathrin-coated Endocytic Vesicles" Molecular Biology of the Cell, vol. 10, 961-974, Apr. 1999.*
Atger et al., "Cyclodextrins as Catalysts for the Removal of Cholesterol from Macrophage Foam Cells" J. Clin. Invest., vol. 99, No. 4, Feb. 1997, 773-780.*
Rapp et al., "Lipids of Human Atherosclerotic Plaques and Xanthomas : Clues to the Mechanism of Plaque Progression" Journal of Lipid Research, vol. 24, pp. 1329-1335, 1983.
Rothblat et al., "Apolipoproteins, Membrane Cholesterol Domains, and the Regulation of Cholesterol Efflux" Journal of Lipid Research, vol. 33, 1992, pp. 1091-1097.
Fielding et al., "Molecular Physiology of Reverse Cholesterol Transport" Journal of Lipid Research, vol. 36, pp. 211-228, 1995.
Miyazaki et al., "Intravenous Injection of Rabbit Apolipoproteins A-I Inhibits the Progression of Atherosclerosis in Cholesterol-Fed Rabbits" Arteriosclerosis, Thrombosis, and Vascular Biology, vol. 15, No. 11, Nov. 1995, pp. 1882-1888.
Badimon et al., "High Density Lipoprotein Plasma Fractions Inhibit Aortic Fatty Streaks in Cholesterol-Fed Rabbits" Lab Invest. Mar. 1989; 60(3): 455-61.
Brown et al., "Lipid Lowering and Plaque Regression" Circulation 1993; 87; 1781-1791.

* cited by examiner

*Primary Examiner*—Robert A Wax
*Assistant Examiner*—Danah Al-Awadi

(57) ABSTRACT

The present disclosure relates to devices methods for the reverse transport of lipids such as cholesterols for the treatment diseases and conditions caused by vulnerable plaques. The devices can reduce or eliminate vulnerable plaques by transporting the plaques away from their location.

12 Claims, 2 Drawing Sheets

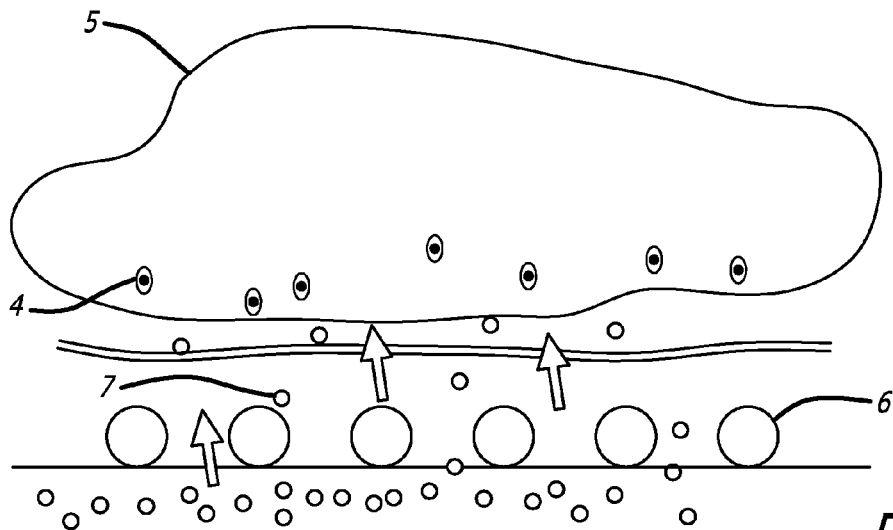
FIG. 2A
FIG. 2B
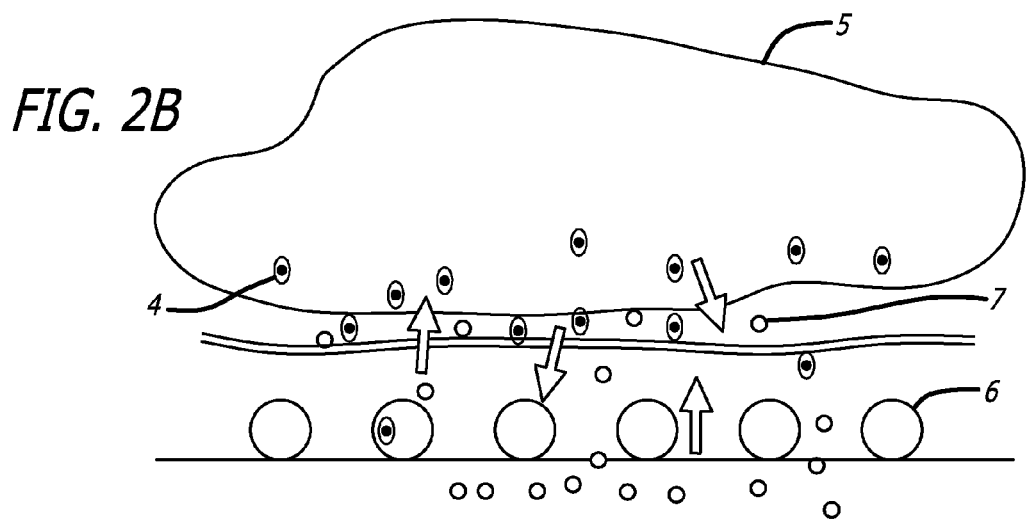
FIG. 2C
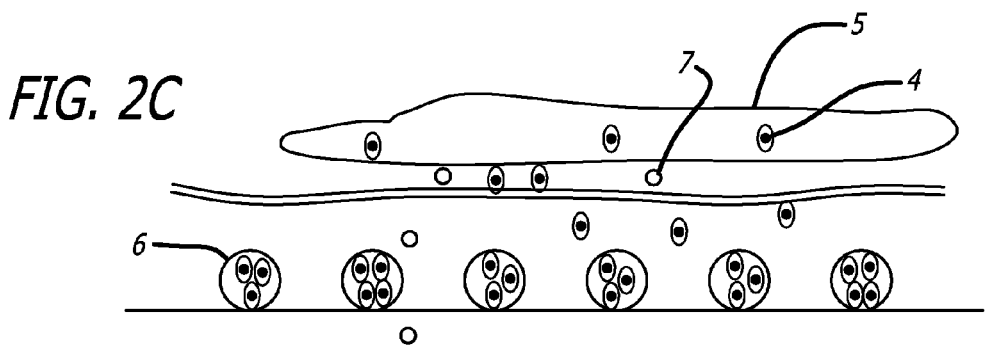

DEVICES AND METHODS FOR REVERSE LIPID TRANSPORT

FIELD OF THE INVENTION

The present disclosure relates to devices and methods for reverse lipid transport useful for eliminating or reducing vulnerable plaques.

BACKGROUND OF THE INVENTION

A vulnerable plaque is an atheromatous plaque which is particularly prone to producing sudden major problems, such as a heart attack or stroke. Generally an atheroma becomes vulnerable if it grows rapidly and has a thin cover separating it from the bloodstream inside the arterial lumen. Tearing of the cover is called plaque rupture.

An atheroma (plural: atheromata) is an accumulation and swelling (-oma) in the artery walls that are made up of cells (mostly macrophage cells), or cell debris, that contain lipids (such as cholesterol and fatty acids), calcium and a variable amount of fibrous connective tissue. In the context of heart or artery matters, atheromata are commonly referred to as atheromatous plaques.

These anatomic lesions usually begin in later childhood and progress over time. Veins may not develop atheromata, unless surgically moved to function as an artery, as in bypass surgery. The accumulation (swelling) is usually between the endothelium lining and the smooth muscle wall central region (media) of the arterial tube. While the early stages, based on gross appearance, have traditionally been termed fatty streaks by pathologists, they are not composed of adipose cells, but of accumulations of white blood cells, especially macrophages that have taken up oxidized low-density lipoprotein (LDL). After they accumulate large amounts of cytoplasmic membranes (with associated high cholesterol content) they are called foam cells. When foam cells die, their contents are released, which attracts more macrophages and creates an extracellular lipid core near the center to inner surface of each atherosclerotic plaque. Conversely, the outer, older portions of the plaque become more calcific, less metabolically active and more physically stiff over time.

Collectively, the process of atheroma development within an individual is called atherogenesis and the overall result of the disease process is termed atherosclerosis. Because artery walls typically enlarge in response to enlarging plaques, these plaques do not usually produce much stenosis of the artery lumen. Therefore, they are not detected by cardiac stress tests or angiography, the tests most commonly performed clinically with the goal of predicting susceptibility to future heart attack. Additionally, because these lesions do not produce significant stenoses, they are typically not considered critical and/or interventionable by interventional cardiologists, even though they may be the more important lesions for producing heart attacks.

In many cases, a vulnerable plaque has a thin fibrous cap and a large and soft lipid pool underlying the cap. These characteristics together with the usual hemodynamic pulsating expansion during systole and elastic recoil contraction during diastole contribute to a high mechanical stress zone on the fibrous cap of the atheroma, making it prone to rupture. Increased hemodynamic stress correlates with increased rates of major cardiovascular events associated with exercise, especially exercise beyond levels an individual does routinely.

The most frequent cause of a cardiac event following rupture of a vulnerable plaque is blood clotting on top of the site of the ruptured plaque that blocks the lumen of the artery, thereby stopping blood flow to the tissues the artery supplies.

Upon rupture, atheroma tissue debris may spill into the blood stream; these debris are often too large to pass on through the capillaries downstream. In this situation, the debris may obstruct smaller downstream branches of the artery resulting in temporary to permanent end artery/capillary closure with loss of blood supply, and death of the previously supplied tissues. A severe case of this can be seen during angioplasty in the slow clearance of injected contrast down the artery lumen. This situation is often termed non-reflow. Additionally, atheroma rupture may allow bleeding from the lumen into the inner tissue of the atheroma making the atheroma size suddenly increase and protrude into the lumen of the artery producing lumen narrowing or even total obstruction. Repeated atheroma rupture and healing is one of the mechanisms, perhaps the dominant one, which creates artery stenosis.

There is an unmet need for devices and methods which remove vulnerable plaques as vulnerable plaques can cause various diseases and conditions such as heart attack and stroke.

SUMMARY OF THE INVENTION

The present disclosure relates to devices and methods for reverse transport of lipids such as cholesterols for the treatment diseases and conditions caused by vulnerable plaques. The devices can reduce or eliminate vulnerable plaques by transporting the plaques away from their location.

One embodiment of the present disclosure relates to a device for reverse lipid transport comprising an apparatus to isolate a plaque region from blood flow, a transfer agent, and a reservoir sink.

In another embodiment, the apparatus is a dual occlusion balloon.

In another embodiment, the transfer agent is a cyclodextrin, a reverse cholesterol transport enhancer, or a chemical transporter.

In another embodiment, the cyclodextrin is methyl-beta-cyclodextrin, beta-cyclodextrin, carboxymethyl-beta-cyclodextrin, or tetradecasulfated-beta-cyclodextrin.

In another embodiment, the reverse cholesterol transport enhancer is selected from the group consisting of high-density lipoprotein (HDL), apolipoprotein A-I (apoA-I), lecithin: cholesterol acyltransferase (LCAT), phospholipid transfer protein (PLTP), hepatic lipase (HL), cholesterol ester transfer protein (CETP), N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF 009.

In another embodiment, the chemical transporter is selected from the group consisting of diethyl ether, monooctanoin, methyl tert-butyl ether, alcohol and halothane; or combinations thereof.

In another embodiment, the halothane is selected from the group consisting of 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

In another embodiment, the reservoir sink is a bound or unbound lipoprotein vesicle, or a lipophilic solution separated by a semi-permeable membrane.

In another embodiment, the lipoprotein vesicle is a phosphatidylcholine vesicle.

In another embodiment, the lipoprotein vesicle has physical dimensions which prevent penetration into a lipid rich lesion through a vessel wall.

The present disclosure also relates to methods of eliminating or reducing vulnerable plaque.

One embodiment of the present disclosure relates to a method of eliminating or reducing vulnerable plaque comprising deploying in a patient a device for reverse lipid transport comprising an apparatus to isolate a plaque region from blood flow, a transfer agent, and a reservoir sink.

In another embodiment of the method of eliminating or reducing vulnerable plaque, the apparatus is a dual occlusion balloon.

In another embodiment of the method of eliminating or reducing vulnerable plaque, the transfer agent is a cyclodextrin, a reverse cholesterol transport enhancer, or a chemical transporter.

In another embodiment of the method of eliminating or reducing vulnerable plaque, the cyclodextrin is methyl-beta-cyclodextrin, beta-cyclodextrin, carboxymethyl-beta-cyclodextrin, or tetradecasulfated-beta-cyclodextrin.

In another embodiment of the method of eliminating or reducing vulnerable plaque, the reverse cholesterol transport enhancer is selected from the group consisting of high-density lipoprotein (HDL), apolipoprotein A-I (apoA-I), lecithin:cholesterol acyltransferase (LCAT), phospholipid transfer protein (PLTP), hepatic lipase (HL), cholesterol ester transfer protein (CETP), N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF 009.

In another embodiment of the method of eliminating or reducing vulnerable plaque, the chemical transporter is selected from the group consisting of diethyl ether, monooctanoin, methyl tert-butyl ether, alcohol and halothane; or combinations thereof.

In another embodiment of the method of eliminating or reducing vulnerable plaque, the haloethane is selected from the group consisting of 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

In another embodiment of the method of eliminating or reducing vulnerable plaque, the reservoir sink is a bound or unbound lipoprotein vesicle, or a lipophilic solution separated by a semi-permeable membrane.

In another embodiment of the method of eliminating or reducing vulnerable plaque, the lipoprotein vesicle is a phosphatidylcholine vesicle.

In another embodiment of the method of eliminating or reducing vulnerable plaque, the lipoprotein vesicle has physical dimensions which prevent penetration into a lipid rich lesion through a vessel wall.

BRIEF DESCRIPTION OF THE DRAWINGS

FIG. 2A, 2B and 2C illustrate how transfer shuttles remove lipids from lipid rich lesions.

DETAILED DESCRIPTION OF THE INVENTION

Figure 1:
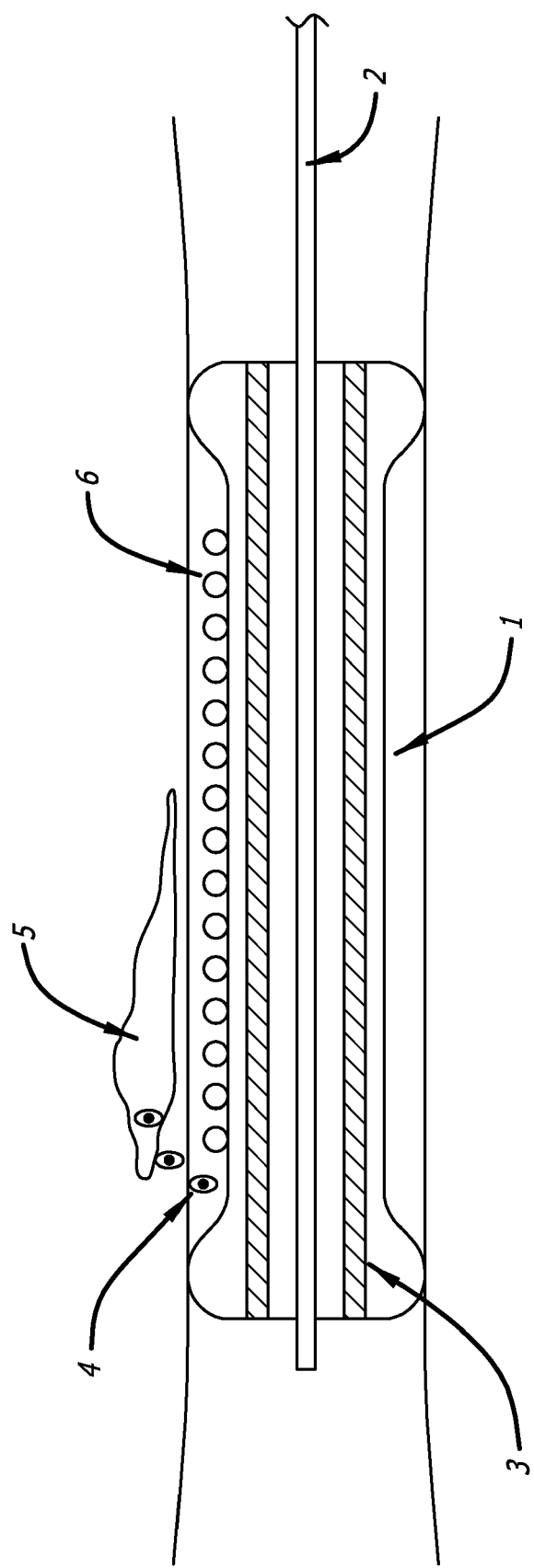
FIG. 1 shows a device for reverse lipid transport having a dual occlusion balloon.

Because of the many diseases or conditions that vulnerable plaques can cause, devices and methods are needed to reduce or eliminate lipids which are significant components of vulnerable plaques. The presently disclosed devices and methods allow for reverse transport of lipids such as cholesterols for treatment of diseases and conditions caused by plaques, especially vulnerable plaques.

One embodiment of the present disclosure relates to a device for reverse lipid transport comprising an apparatus to isolate a plaque region from blood flow, a transfer agent, and a reservoir sink.

In another embodiment, the apparatus is a dual occlusion balloon.

In another embodiment, the transfer agent is a cyclodextrin, a reverse cholesterol transport enhancer, or a chemical transporter.

In another embodiment, the cyclodextrin is methyl-beta-cyclodextrin, beta-cyclodextrin, carboxymethyl-beta-cyclodextrin, or tetradecasulfated-beta-cyclodextrin.

In another embodiment, the reverse cholesterol transport enhancer is selected from the group consisting of high-density lipoprotein (HDL), apolipoprotein A-I (apoA-I), lecithin:cholesterol acyltransferase (LCAT), phospholipid transfer protein (PLTP), hepatic lipase (HL), cholesterol ester transfer protein (CETP), N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF 009. Niastin/LTZX-2626 is a high density lipoprotein (HDL) cholesterol increasing agent. ETC-216/Recombinant ApoA-I Milano-phospholipid complex is an HDL-cholesterol increasing agent. It is a variant of apoliprotein A-I (apo A-I), the major protein of HDL. The mechanism of AIM as a human recombinant protein complexed to phospholipid is to mimic HDL and its function by removing cholesterol and other lipids from tissues including arterial walls and transporting them to the liver for elimination. Ibrolipim/NO-1886/OPF-009 is a HDL-cholesterol increasing agent developed for the treatment of lipoprotein disorders. The chemical structure of Ibrolipim/NO-1886/OPF-009 is:

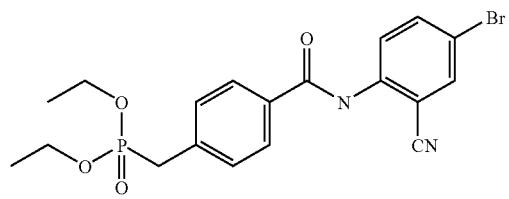

HDL-376 is also a HDL-cholesterol increasing agent. The chemical structure of HDL-376 is:

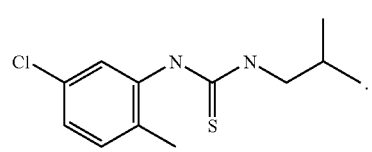

In another embodiment, the chemical transporter is selected from the group consisting of diethyl ether, monooctanoin, methyl tert-butyl ether, alcohol and halothane; or combinations thereof.

In another embodiment, the halothane is selected from the group consisting of 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

In another embodiment, the reservoir sink is a bound or unbound lipoprotein vesicle, or a lipophilic solution separated by a semi-permeable membrane.

In another embodiment, the lipoprotein vesicle is a phosphatidylcholine vesicle.

In another embodiment, the lipoprotein vesicle has physical dimensions which prevent penetration into a lipid rich lesion through a vessel wall.

The present disclosure also relates to methods of eliminating or reducing vulnerable plaque.

One embodiment of the present disclosure relates to a method of eliminating or reducing vulnerable plaque comprising deploying in a patient a device for reverse lipid transport comprising an apparatus to isolate a plaque region from blood flow, a transfer agent, and a reservoir sink.

In another embodiment of the method of eliminating or reducing vulnerable plaque, the apparatus is a dual occlusion balloon.

In another embodiment of the method of eliminating or reducing vulnerable plaque, the transfer agent is a cyclodextrin, a reverse cholesterol transport enhancer, or a chemical transporter.

In another embodiment of the method of eliminating or reducing vulnerable plaque, the cyclodextrin is methyl-beta-cyclodextrin, beta-cyclodextrin, carboxymethyl-beta-cyclodextrin, or tetradecasulfated-beta-cyclodextrin.

In another embodiment of the method of eliminating or reducing vulnerable plaque, the reverse cholesterol transport enhancer is selected from the group consisting of high-density lipoprotein (HDL), apolipoprotein A-I (apoA-I), lecithin:cholesterol acyltransferase (LCAT), phospholipid transfer protein (PLTP), hepatic lipase (HL), cholesterol ester transfer protein (CETP), N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF 009.

In another embodiment of the method of eliminating or reducing vulnerable plaque, the chemical transporter is selected from the group consisting of diethyl ether, monooctanoin, methyl tert-butyl ether, alcohol and halothane; or combinations thereof.

In another embodiment of the method of eliminating or reducing vulnerable plaque, the haloethane is selected from the group consisting of 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

In another embodiment of the method of eliminating or reducing vulnerable plaque, the reservoir sink is a bound or unbound lipoprotein vesicle, or a lipophilic solution separated by a semi-permeable membrane.

In another embodiment of the method of eliminating or reducing vulnerable plaque, the lipoprotein vesicle is a phosphatidylcholine vesicle.

In another embodiment of the method of eliminating or reducing vulnerable plaque, the lipoprotein vesicle has physical dimensions which prevent penetration into a lipid rich lesion through a vessel wall.

When deployed, the blood flow in a patient is blocked and transfer agents are delivered to the localized region of the lipid rich lesion. FIG. 1 shows a device for reverse lipid transport including a dual occlusion balloon. The device can be deployed in a patient. It can be positioned inside a lumen with the help of a catheter shaft 2. A blood perfusion lumen 3 through the balloon can maintain blood flow during the deployment procedure. Transfer agents can be bound to the surface of a dual occlusion balloon 1. A transfer agent containing a lipid from the lipid rich atherosclerotic region is represented by 4. Reservoir sinks 6 such as unilamellar vesicles of phosphatidylcholine can capture the transfer agents. This process can eliminate or reduce the lipid rich atherosclerotic lesion 5.

FIG. 2A-2C show how transfer agents remove lipids from lipid rich atherosclerotic lesions 5. Transfer agents such as high density lipoprotein or cyclodextrin can be released through an apparatus to isolate a plaque region from blood flow such as a dual occlusion balloon catheter 1. A transfer agent containing a lipid from the lipid rich atherosclerotic region is represented by 4. A transfer agent which does not yet contain a lipid from the lipid rich atherosclerotic region is represented by 7. The release can be made, for example, through a weeping balloon. or ports in a lumen. The transfer agents can move, for example, by diffusion into the lipid rich lesion 5 (see FIG. 2A). The arrows in FIG. 2A show movement of the transfer agents.

FIG. 2B shows how transfer agents can absorb lipids such as cholesterol and/or cholesterol like substances and carry these lipids away from a lesion. The arrows show movement of the transfer agents to and from the lipid rich atherosclerotic lesions 5. Transfer agents which have been bound with lipid molecule(s) can move back into the dual occlusion balloon into reservoir sinks 6.

FIG. 2C shows how lipid saturated transfer agents 4 can be captured by reservoir sinks 6 such as liposinks bound to a catheter system. In this way, the captured lipids can be cleared from the lesion 5.

The presently disclosed device for reverse lipid transport includes an apparatus to isolate a plaque region from blood flow. Such an apparatus can deliver transfer agents which can carry lipids away from a lipid rich lesion and allow movement back to a reservoir sink to carry the saturated transfer agents away from the lesion. One example of such a device is a dual occlusion balloon. The dual occlusion balloon may contain a catheter shaft which can be used to position the dual occlusion balloon to the lipid rich plaque region. The apparatus may contain a blood perfusion lumen which allows maintenance of blood flow during a deployment procedure.

The presently disclosed device for reverse lipid transport includes a transfer agent. This transfer agent allows for reverse lipid transport by binding to lipid in a lipid rich lesion such as an atherosclerotic lesion. One example of such a transfer agent is cyclodextrin. Cyclodextrins (sometimes called cycloamyloses) make up a family of cyclic oligosaccharides, composed of 5 or more α-D-glucopyranoside units linked as in amylose (a fragment of starch). The 5-membered macrocycle is not natural. The largest well-characterized cyclodextrin contains 32 1,4-anhydroglucopyranoside units, while as a poorly characterized mixture, even at least 150-membered cyclic oligosaccharides are also known. Typical cyclodextrins contain a number of glucose monomers ranging from six to eight units in a ring, creating a cone shape. Cyclodextrins are able to form host-guest complexes with hydrophobic molecules given the unique nature imparted by their structure. As a result these molecules have found a number of applications in a wide range of fields. Cyclodextrins can effectively immobilize inside their rings toxic compounds, such as trichloroethane or heavy metals, or can form complexes with stable substances, such as trichlorfon (an organophosphorus insecticide) enhancing their decomposition. Examples of cyclodextrins which can serve as the transfer agents of the present disclosure are, but not limited to: methyl-beta-cyclodextrin, beta-cyclodextrin, carboxymethyl-beta-cyclodextrin, and tetradecasulfated-beta-cyclodextrin.

The presently disclosed transfer agents can be for example, a reverse cholesterol transport enhancer. Reverse cholesterol transport enhancers enhance reverse cholesterol transport. Reverse cholesterol transport (RCT) is a pathway by which accumulated cholesterol is transported from a vessel wall to the liver for excretion, thus preventing atherosclerosis. Major constituents of RCT include acceptors such as high-density lipoprotein (HDL) and apolipoprotein A-I (apoA-I), and enzymes such as lecithin:cholesterol acyltransferase (LCAT), phospholipid transfer protein (PLTP), hepatic lipase (HL) and cholesterol ester transfer protein (CETP). A critical part of RCT is cholesterol efflux, in which accumulated cholesterol is removed from macrophages in the subintima of the vessel wall by ATP-binding membrane cassette transporter A1 (ABCA1) or by other mechanisms, including passive diffusion, scavenger receptor B1 (SR-B1), caveolins and sterol 27-hydroxylase, and collected by HDL and apoA-I. Esterified cholesterol in the HDL is then delivered to the liver for excretion. In patients with mutated ABCA1 genes, RCT and cholesterol efflux are impaired and atherosclerosis is increased. In studies with transgenic mice, disruption of ABCA1 genes can induce atherosclerosis. Levels of HDL are inversely correlated with incidences of cardiovascular disease. Supplementation with HDL or apoA-I can reverse atherosclerosis by accelerating RCT and cholesterol efflux. On the other hand, pro-inflammatory factors such as interferon-gamma (IFN-$\gamma$), endotoxin, tumor necrosis factor-alpha (TNF-$\alpha$) and interleukin-1 beta (IL-1$\beta$), can be atherogenic by impairing RCT and cholesterol efflux. RCT and cholesterol efflux play a major role in anti-atherogenesis, and modification of these processes may provide new therapeutic approaches to cardiovascular disease. This is done by binding lipid molecules to the reverse cholesterol transport enhancers. Examples of reverse cholesterol transport enhancers are high-density lipoprotein (HDL), apolipoprotein A-I (apoA-I), and enzymes such as lecithin:cholesterol acyltransferase (LCAT), phospholipid transfer protein (PLTP), hepatic lipase (HL) and cholesterol ester transfer protein (CETP). More examples reverse transport enhancers include N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF009.

The presently disclosed transfer agent can be a chemical transporter. Examples of chemical transporters of the present disclosure include but are not limited to diethyl ether, monooctanoin, methyl tert-butyl ether (MtBE), alcohols, halothane, halothane, halothane/MtBE combination, MtBE/alcohol combinations; and combinations thereof.

The addition of MtBE to halothane can enhance halothane's ability to serve as a chemical transporter of lipids. Examples of halothanes which can be used are 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

Neutral lipids generally can be extracted with relatively non-polar solvents such as diethyl ether. Therefore, diethyl ether can serve as a chemical transporter to facilitate reverse lipid transport. Monooctanoin is a semisynthetic glycerol derivative generally used to dissolve cholesterol stones in the common and intrahepatic bile ducts. Monooctanoin's lipid binding properties can be used to serve as a chemical transport of the presently disclosed device.

The reservoir sinks of the presently disclosed device can be a lipoprotein vesicle. The lipoprotein vesicles can be bound or unbound. The unbound lipoprotein vesicles can have physical dimensions that prevent them from penetrating into the lipid rich lesion through the vessel wall. Following deployment or intervention using the presently disclosed device, vesicles can then be transported downstream to be eventually cleared from the body trough the liver or other means.

An example of a lipoprotein vesicle which can be used is a phosphatidylcholine vesicle. A lipid vesicle is a spherical vesicle composed of a bilayer membrane which refers to a membrane composed of a phospholipid and cholesterol bilayer. Liposomes can be composed of naturally-derived phospholipids with mixed lipid chains (such as phosphatidylethanolamine), or of pure surfactant components such as DOPE (dioleoylphosphatidylethanolamine). Lipid vesicles, can but not always, contain a core of aqueous solution. Lipid spheres that contain no aqueous material are called micelles.

Additional reservoir sinks of the present disclosure include lipophilic solutions which are separated by semi-permeable membranes permitting transport of transfer agents. Also, generally, the reservoir sink can be an organic chemical system that is immiscible with aqueous surrounding in the vessel.

Some of the advantages of the present devices are that the reverse lipid transport does not require a permanent implant, that cyclodextrines have been shown to be nontoxic to cells at 10 mM concentrations, and phosphatidylcholine vesicles have been shown to be nontoxic to cells at 10 mg/ml concentrations.

The devices for lipid transport of the present disclosure can be used to reduce or eliminate vulnerable plaque. Vulnerable plaque can cause diseases or conditions which are characterized by the build-up of fatty deposits called atherosclerotic plaque in the walls of blood vessels. The rupture of this plaque can cause the formation of a blood clot that blocks the flow of blood to the heart or the brain, often resulting in a heart attack or stroke.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A device for reverse lipid transport of lipids from a lipid rich atherosclerotic plaque region to a bound phosphatidylcholine vesicle comprising a dual occlusion balloon to isolate said plaque region from blood flow deployed in vivo, a transfer agent releasably bound to said dual occlusion balloon wherein said transfer agent is cyclodextrin, a reverse cholesterol transport enhancer, or a chemical transporter, and said phosphatidylcholine vesicle is bound to said dual occlusion balloon.

2. The device of claim 1, wherein said cyclodextrin is methyl-beta-cyclodextrin, beta-cyclodextrin, carboxymethyl-beta-cyclodextrin, or tetradecasulfated-beta-cyclodextrin.

3. The device of claim 1, wherein said reverse cholesterol transport enhancer is selected from the group consisting of high-density lipoprotein (HDL) apolipoprotein A-I (apoA-I), lecithin:cholesterol acyltransferase (LCAT), phospholipid transfer protein (PLTP), hepatic lipase (HL), cholesterol ester transfer protein (CETP), N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF-009.

4. The device of claim 1, wherein said chemical transporter is selected from the group consisting of diethyl ether, monooctanoin, methyl tert-butyl ether, alcohol and halothane; or combinations thereof.

5. The device of claim 4, wherein said halothane is selected from the group consisting of 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

6. The device of claim 1, wherein said lipoprotein vesicle has physical dimensions which prevent penetration into a lipid rich lesion through a vessel wall.

7. A method of eliminating or reducing vulnerable plaque comprising deploying in a patient a device for reverse lipid transport of lipids from a lipid rich atherosclerotic plaque region to a bound phosphatidylcholine vesicle comprising a dual occlusion balloon to isolate said plaque region from blood flow deployed in vivo, a transfer agent releasably bound to said dual occlusion balloon wherein said transfer agent is cyclodextrin, a reverse cholesterol transport enhancer, or a chemical transporter, and said phosphatidylcholine vesicle is bound to said dual occlusion balloon.

8. The method of claim 7, wherein said cyclodextrin is methyl-beta-cyclodextrin, beta-cyclodextrin, carboxymethyl-beta-cyclodextrin, or tetradecasulfated-beta-cyclodextrin.

9. The method of claim 7, wherein said reverse cholesterol transport enhancer is selected from the group consisting of high-density lipoprotein (HDL) apolipoprotein A-I (apoA-I), lecithin:cholesterol acyltransferase (LCAT), phospholipid transfer protein (PLTP), hepatic lipase (HL), cholesterol ester transfer protein (CETP), N-Acetyl-D-glutamyl-3,3-diphenyl-D-alanyl-D-argininamide, Niastin/LTZX-2626, HDL-376, ETC-216/Recombinant ApoA-I Milano-phospholipid complex, and Ibrolipim/NO-1886/OPF-009.

10. The method of claim 7, wherein said chemical transporter is selected from the group consisting of diethyl ether, monooctanoin, methyl tert-butyl ether, alcohol and halothane; or combinations thereof.

11. The method of claim 10, wherein said wherein said halothane is selected from the group consisting of 2-bromo-2-chloro-1,1,1-trifluoroethane, 2-chloro-1,2-dibromo-1,1,2-trifluoroethane, 1-bromo-2-chloro-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4-tetrachlorobutane, 1,1,1-trichlorotrifluoroethane, and 1,2-dibromo-tetrafluoroethane.

12. The method of claim 7, wherein said lipoprotein vesicle has physical dimensions which prevent penetration into a lipid rich lesion through a vessel wall.

* * * * *